United States Patent [19]

Cotter

[11] Patent Number: 5,461,037
[45] Date of Patent: Oct. 24, 1995

[54] LIPID EMULSION

[75] Inventor: Richard Cotter, Libertyville, Ill.

[73] Assignee: Clintec Nutrition Company, Deerfield, Ill.

[21] Appl. No.: 213,451

[22] Filed: Mar. 14, 1994

Related U.S. Application Data

[63] Continuation of Ser. No. 981,934, Nov. 23, 1992, abandoned, which is a continuation of Ser. No. 503,068, Mar. 29, 1990, abandoned, which is a continuation of Ser. No. 348,190, May 8, 1989, abandoned, which is a continuation of Ser. No. 41,165, Apr. 22, 1987, abandoned, which is a continuation-in-part of Ser. No. 787,741, Oct. 15, 1985, Pat. No. 4,678,808.

[51] Int. Cl.$^6$ .................. A61K 31/685; A61K 31/23; B01J 13/00
[52] U.S. Cl. ............. 514/78; 252/309; 252/312; 514/552; 514/938
[58] Field of Search ...................... 252/309, 312; 514/78, 552

[56] References Cited

FOREIGN PATENT DOCUMENTS

60215/86  2/1987  Australia .

OTHER PUBLICATIONS

Carpentier et al, *Parameters for Evaluation of Lipid Metabolism*, Journal of Parenteral and Enteral Nutrition, vol. 11, No. 5 (Suppl.), pp. 104S–108S (1987).
Carpentier et al, *Interactions between Exogenous Fat and Plasma/Lipoproteins*, Infusionstherapie 14:suppl. 3, pp. 29–32 (1987).
Untracht, *Intravascular Metabolism of an Artificial Transporter of Triacylglycerols/Alterations of Serum Lipoproteins Resulting from Total Parenteral Nutrition with Intralipid*, Biochimica et Biophysica Acts, 711, 176–192 (1982).
Griffin et al, *Appearance and Characterization of Lipoprotein X during Continuous Intralipid Infusions, in the Neonate*, J. Clin. Invest. vol. 64, pp. 1703–1712 (1979).
Haumont et al., *Tolerance of Premature Infants to 10 and 20% 8th Congress of the European Society of Parenteral and Enteral Nutrition, vol. 8, No. 5 (1984)*.
Tashiro et al, *Alteration of Lipoprotein Profile during Total Parenteral Nutrition with Intralipid 10%*, Journal of Parenteral and Enteral Nutrition, vol. 10, No. 6, pp. 62214 626 (1986).
Rigaud et al, *Quantification of Lipoprotein X and its Relationship to Plasma Lipid Profile during Different Types of Parenteral Nutrition*, Journal of Parenteral and Enteral Nutrition, vol. 8, No. 5, pp. 529–534 (1984).
Carpentier et al, *Effects of Infusion Rate and Phospholipid Content of Fat Emulsions in Man*, Clinical Nutrition, 5 (Suppl.) p. 43 (1986).

*Primary Examiner*—Richard D. Lovering
*Attorney, Agent, or Firm*—Hill, Steadman & Simpson

[57] ABSTRACT

A lipid emulsion is provided comprising water, an emulsifier, and a glyceride oil component. The weight ratio of the emulsifier to glyceride oil is approximately 0.04 to about 0.01. It has been found that intravenous lipid emulsions having a weight ratio of emulsifier to glyceride oil of approximately 0.04 to about 0.01 are more rapidly metabolically utilized.

6 Claims, 3 Drawing Sheets

LIPID EMULSION

This is a continuation of Ser. No. 07/981,934, filed Nov. 23, 1992, now abandoned, which is a continuation of Ser. No. 07/503,068, filed Mar. 29, 1990, now abandoned, which is a continuation of Ser. No. 07/348,190, filed May 8, 1989, now abandoned, which is a continuation of Ser. No. 07/041,165, filed Apr. 22, 1987, now abandoned, which is a continuation-in-part of Ser. No. 06/787,741, filed Oct. 15, 1985, now U.S. Pat. No. 4,678,808.

BACKGROUND OF THE INVENTION

The present invention relates generally to lipid emulsion systems. Specifically, the present invention relates to lipid emulsion systems for intravenous infusion.

It is known to intravenously infuse lipid emulsions into patients. Typically, lipid emulsions comprise: an aqueous environment; an emulsifier; and a glyceride oil component. Present commercial lipid emulsions, such as, for example, TRAVAMULSION, INTRALIPID, and LYPOSYN, utilize an excess amount of phospholipids as an emulsifier in their formulations. For example, these formulations typically have a phospholipid to glyceride oil ratio, by weight, of approximately 0.12 to 0.06. The excess phospholipids result in a fraction of the expected emulsion vesicles as well as a single and multilamellar liposome fraction.

As stated above, these lipid emulsions are designed to be infused into a patient. Because of the use of excess phospholipids, removal of the lipid emulsions from the blood stream may not proceed at a sufficiently fast rate. It is believed that removal of the emulsion particles from the blood stream is by a pathway having a half life (T ½) of up to approximately 1 hour. However, removal of the liposome particles from the blood stream is by another pathway, having an extremely long T ½ of 2 days. (See Untracht, S. H., *Intravascular Metabolism of an Artificial Transporter of Triacylglycerols*, Biochem Biophys Acta 711(1): 176–92, 1982.) Because the liposome particles are removed from the blood stream via this second pathway that has a long T ½ hyperlipidemia is observed in many patients after parenteral lipid emulsion infusions. The inventor of the present invention believes that it is the liposomes, that use the longer T ½ pathway, that produce the hyperlipidemia observed in patients who receive lipid emulsion infusions.

Hyperlipidemia is a condition wherein the patient has too much lipid in his blood. This results in an increase in the risk of cardio-vascular disease, gastrointestinal disturbances, heptosplenomegaly, impaired hepatic function, anemia, thromobocytopenia, prolonged clotting time, spontaneous bleeding, and respiratory complications. This is especially true in neonates and infants, wherein hyperlipidemia is a dangerous condition that can cause respiratory failure. Indeed, many doctors will not prescribe lipid emulsions for neonates and infants due to the fear of hyperlipidemia and accompanying respiratory failure.

SUMMARY OF THE INVENTION

It has been found that lipid emulsion made using a reduced phospholipid to oil weight ratio at the critical concentration, i.e., the concentration where the amount necessary for complete emulsification of the glyceride oil with the emulsifier takes place, greatly reduces the liposomal content and thus avoids hyperlipidemia in patients.

The present invention provides a lipid emulsion for nutritional support of a patient, as well as, a lipid emulsion system for delivering therapeutic agents. The lipid emulsion comprises water, an emulsifier, and a glyceride oil component. The weight ratio of the emulsifier to glyceride oil is approximately 0.04 to about 0.01. It has been found that intravenous lipid emulsion having a weight ratio of emulsifier to glyceride oil of approximately 0.04 to about 0.01 are more rapidly metabolically utilized.

The rapid bioavailability of lipid emulsions creates immediate biological effects and makes them attractive vehicles for acute intravenous therapies. Further studies have also shown that by reducing the phospholipid composition of the emulsion to about 0.4–0.6% a more rapid bioavailability is produced. This rapid bioavailability is produced by creating a more attractive lipid particle for apolipoprotein transfer from high density lipoproteins found in circulating blood. Such apopolipoproteins are essential for control of lipid emulsion endothelial receptor binding and activation of hydrolytic enzymes at these receptor sites. The reduction in phospholipids in such emulsions results in a more rapid delivery of the emulsion to metabolism and a release of the biologically active metabolic products. This brings about a rapid biological response to these therapies.

Preferably, the emulsifier is a phospholipid. The glyceride oil can be mono-, di-, or tri-. Preferably, the lipid emulsion includes an osmotic agent. Preferably, the osmotic agent can include, for example, glycerol, glucose, xylitol, or sorbitol. Preferably, a sufficient amount of an osmotic agent is used to produce a solution with a final osmolarity of approximately 280 to about 300 milliosmoles.

Accordingly, an advantage of the present invention is to provide an improved lipid emulsion system.

Another advantage of the present invention is that it provides a more rapidly metabolized lipid nutritional supply.

A further advantage of the present invention is that it provides a lipid emulsion system for delivering lipid soluble drugs.

A still further advantage of the present invention is that it provides a lipid emulsion that reduces the risk of hyperlipidemia in patients who receive the lipid emulsion.

Additional features and advantages of the present invention are described in, and will be apparent from, the detailed description of the presently preferred embodiments and from the drawings.

DETAILED DESCRIPTION OF THE PRESENTLY PREFERRED EMBODIMENT

Figure 1:
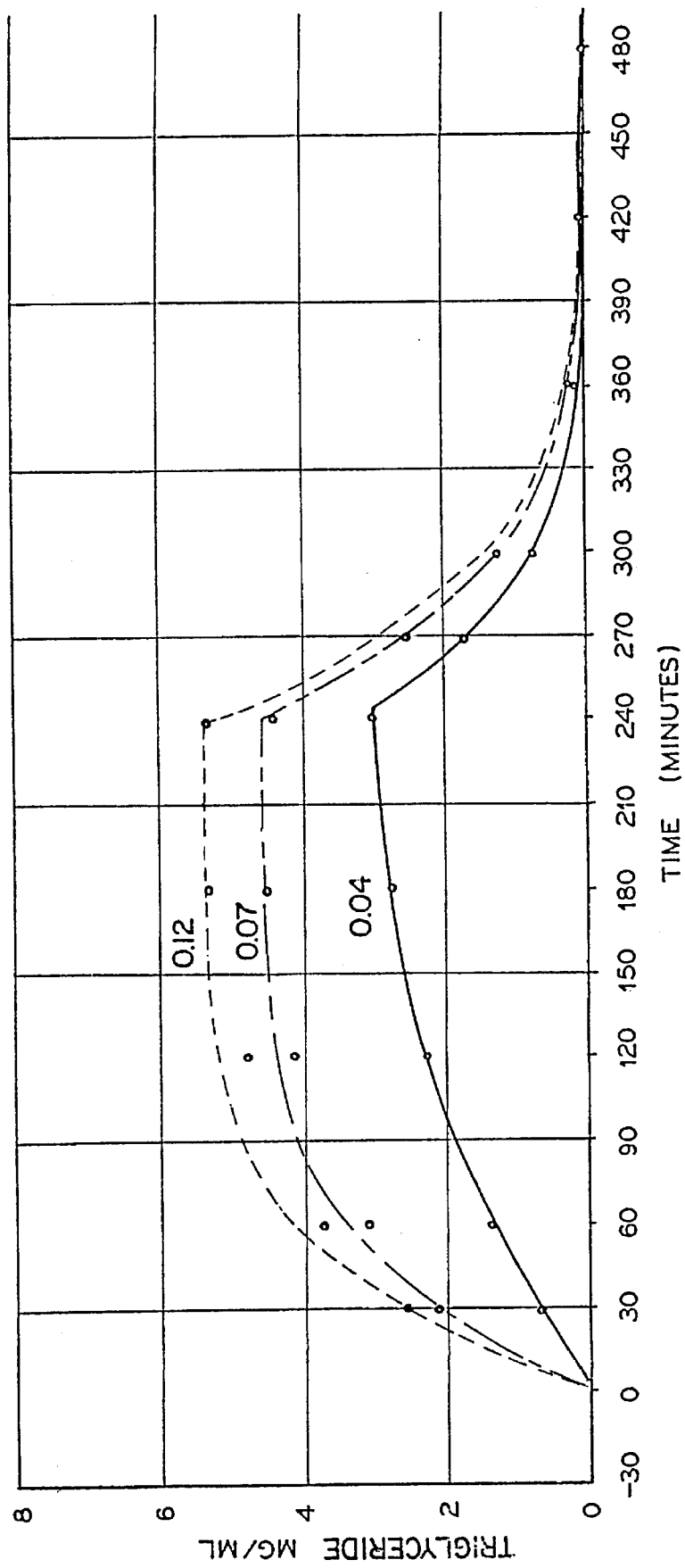
FIG. 1 illustrates the emulsion kinetics at different phospholipid to oil ratios through a plot of the plasma triglyceride concentration versus time.

The present invention provides a lipid emulsion for nutritional support, as well as, a lipid emulsion system for delivering a therapeutic agent. The lipid emulsion includes an emulsifier, a glyceride oil component, an aqueous environment, and preferably an osmotic agent. Preferably, the emulsifier is a phospholipid. Preferably, the phospholipid is chosen from the group consisting of egg phosphatides, soybean phosphatides, or phosphatides of marine origin.

Although the oil can be a mono-, di-, or tri-, glyceride, preferably, the oil is triglyceride. Preferably the triglyceride oil is chosen from the group consisting of soybean, safflower, marine, black currant seed, borage oil, palm kernel oil, or coconut oil. Preferably the lipid emulsion contains approximately 10 to about 50% by weight oil. Preferably, the osmotic agent is chosen from the group consisting of glycerol, glucose, sorbitol, or xylitol. Preferably, sufficient osmotic agent is used so that a solution with a final osmolarity of approximately 280 to about 300 milliosmoles is achieved.

The emulsifier to triglyceride oil weight ratio of the lipid emulsion of the present invention is equal to or less than approximately 0.04. Preferably the emulsifier to triglyceride weight ratio is approximately 0.04 to about 0.01. As set forth in detail below, by utilizing a low emulsifier to triglyceride oil ratio a greatly reduced liposomal content is observed with a reduction of risk of hyperlipidemia in patients. Due to the reduction in liposomal content, a more rapidly metabolized lipid emulsion is achieved.

The lipid emulsions are recommended clinically for nutritional support to be used at dosages up to 2.5 g/kg/24 hours for adults and up to 4 g/kg/24 hours for children. However, the dosage levels of these emulsions are recommendations and each patient must be monitored for the build up of emulsions and free fatty acids during infusion to assure the safety of such therapies.

By way of example, and not limitation, examples of the present invention will now be set forth to illustrate the advantages of using a lipid emulsion having a low phospholipid to oil weight ratio, i.e. a ratio equal to or below 0.04. The metabolism of three types of 10% intravenous lipid emulsion was evaluated using TRAVAMULSION® available from Travenol Laboratories, Inc., Deerfield, Ill. The emulsions were prepared with different phospholipid to triglyceride oil ratios and then infused into beagle dogs. In addition to infusing only lipids, the three emulsions were mixed with amino acids and dextrose to determine their stability in a typical total parenteral nutrition (TPN) formulation. The TPN solutions were also infused into beagles.

The 10% intravenous lipid emulsions evaluated were: 10% TRAVAMULSION with 1.2% egg phosphatide (0.12 phospholipid to oil ratio); 10% TRAVAMULSION with 0.7% egg phosphatide (0.07 phospholipid to oil ratio); and 10% TRAVAMULSION with 0.4% egg phosphatide (0.04 phospholipid to oil ratio). As stated above, to determine their stability in a TPN regime, the lipid emulsions were also mixed with dextrose and amino acids. The dextrose was a 10% dextrose solution and the amino acids solution was 8.5% TRAVASOL® with electrolytes available from Travenol Laboratories, Inc., Deerfield, Ill.

Three male beagle dogs weighing approximately 7 to 13 kg were used in the study. The animals were obtained and housed in accordance with Good Laboratory Practices.

Phase 1 of the study was conducted over a three week period wherein the three male beagle dogs were infused with a lipid emulsion, for a four-hour period, for three consecutive days each week. All the dogs were infused with a 10% intravenous lipid emulsion at a lipid dose of 2 g/kg. During week one: beagle 102-4 received a lipid emulsion containing a 0.04 phospholipid to oil weight ratio; beagle 110-4 received a lipid emulsion containing a 0.07 phospholipid to oil weight ratio; and beagle 111-4 received a lipid emulsion containing a 0.12 phospholipid to oil weight ratio. During week 2: beagle 110-4 received a lipid emulsion having a 0.04 phospholipid to oil ratio; beagle 111-4 received a lipid emulsion having a 0.07 phospholipid to oil ratio; and beagle 102-4 received a lipid emulsion having a 0.12 phospholipid to oil ratio. During week three: beagle 111-4 received a lipid emulsion having a 0.04 phospholipid to oil ratio; beagle 102-4 received a lipid emulsion having a 0.07 phospholipid to oil ratio; and beagle 110-4 received a lipid emulsion having a 0.12 phospholipid to oil ratio. Accordingly, at the end of the three week study, each dog received each of the three lipid emulsions. (Phase 1 is summarized in Table I below.)

TABLE I

| | PHASE 1 10% TRAVAMULSION | | | | | |
|---|---|---|---|---|---|---|
| | 0.04 Phospholipid:Oil | | | 0.07 Phospholipid:Oil | | |
| | Day 1 | Day 2 | Day 3 | Day 1 | Day 2 | Day 3 |
| Week 1 | Dog 102-4 | Dog 102-4 | Dog 102-4 | Dog 110-4 | Dog 110-4 | Dog 110-4 |
| Week 2 | Dog 110-4 | Dog 110-4 | Dog 110-4 | Dog 111-4 | Dog 111-4 | Dog 111-4 |
| Week 3 | Dog 111-4 | Dog 111-4 | Dog 111-4 | Dog 102-4 | Dog 102-4 | Dog 102-4 |
| | 0.12 Phospholipid:Oil | | | | | |
| | Day 1 | | Day 2 | | Day 3 | |
| Week 1 | Dog 111-4 | | Dog 111-4 | | Dog 111-4 | |
| Week 2 | Dog 102-4 | | Dog 102-4 | | Dog 102-4 | |
| Week 3 | Dog 110-4 | | Dog 110-4 | | Dog 110-4 | |

Blood samples (approximately 5 ml) were taken from the dogs during and after the lipid emulsion infusions at 0, 0.5, 1, 2, 3, 4, 4.5, 5, 6, 7, 8, and 72 hours after the start of lipid emulsion infusions. The serum was analyzed for triglyceride content by nephelometry and an aliquot of serum was submitted to the Clinical Laboratory Services of Travenol Laboratories for measurement of the phospholipid content.

Phase 2 of the evaluation involved an additional week of testing. The same three beagle dogs were infused, for a four-hour period, for three consecutive days with a three in one solution of a lipid, protein, and carbohydrate at a lipid dose of 2 g/kg each. During this additional week, beagle 102-4 received a three in one solution having 0.04 egg phospholipid to oil weight ratio; beagle 110-4 received a three in one solution having 0.07 egg phospholipid to oil weight ratio; and beagle 111-4 received a three in one solution having a 0.12 egg phospholipid to oil weight ratio. (Phase 2 is summarized in Table II below.) As in Phase 1, blood samples were taken from the dogs and analyzed for triglyceride and phospholipid content.

TABLE II

| | PHASE 1 10% TRAVAMULSION | | |
|---|---|---|---|
| Solution | Day 1 | Day 2 | Day 3 |
| 0.04 Phospholipid:Oil | Dog 102-4 | Dog 102-4 | Dog 102-4 |
| 0.07 Phospholipid:Oil | Dog 110-4 | Dog 110-4 | Dog 110-4 |
| 0.12 Phospholipid:Oil | Dog 111-4 | Dog 111-4 | Dog 111-4 |

The values for the triglyceride concentration in the blood of the beagles were analyzed using a mathematical model designed to evaluate the kinetics of emulsion metabolism. A plot of triglyceride concentration vs time is illustrated in FIG. 1. In FIG. 1 the plot points were determined by plotting the observed valves for all the readings and determining the mean—the lipid emulsion with a 0.04 phospholipid to oil weight ratio is represented by a solid line; the lipid emulsion with a 0.07 phospholipid to oil weight ratio is represented by a sectional line; and the lipid emulsion with 0.12 phospholipid to oil weight ratio is represented by a dotted line. The analysis is summarized below. A number of kinetic parameters indicative of metabolism were evaluated and are indicated. Table III sets forth the geometric means for the kinetic parameters during the infusion period.

TABLE III

Statistical Comparison of Kinetic Parameters

| | Kinetic Parameter | Phospholipid to Oil Ratios | | |
|---|---|---|---|---|
| | | 0.04 | 0.07 | 0.12 |
| Infusion Phase | BL | 0.000 | 0.000 | 0.002 |
| | SS | 3.12 | 4.54 | 5.36 |
| | MPR | 0.024 | 0.073 | 0.089 |
| | THM | 70.7 | 33.9 | 32.8 |
| Elimination Phase | EIC | 3.20 | 4.49 | 5.03 |
| | MMP | 0.94 | 1.31 | 0.96 |
| | MER | 0.055 | 0.070 | 0.077 |
| | HL | 20.1 | 22.0 | 22.6 |
| | THI | 31.9 | 34.9 | 35.8 |
| | TBL | 254 | 290 | 270 |

| | Kinetic Parameter | Statistical Comparison (a = 0.05) |
|---|---|---|
| Infusion Phase | BL | NS |
| | SS | NS |
| | MPR | L < M, H |
| | THM | NS |
| Elimination Phase | EIC | NS |
| | MMP | NS |
| | MER | NS |
| | HL | NS |
| | THI | NS |

BL = base line value of triglyceride before infusion.
SS = steady state levels of triglyceride.
MPR = maximum pick up rate - initial rate of increase of triglyceride at early time points.
THM = time to reach ½ steady state.
EIC = elimination phase initial concentration.
MMP = Michaelis-Menten parameter concentration at which the elimination rate if half maximum.
MER = maximum elimination rate - elimination rate at beginning of the elimination period.
HL = half life in the first order region of the elimination period.
THI = time to reach half of the initial concentration.
TBL = time to reach the baseline value.
NS = Not Significant
L = Low P:O Ratio
M = Medium P:O Ratio
H = High P:O Ratio Statistical analysis reveals that the maximum pick-up rate, i.e. the initial rate of increase, in triglyceride level was significantly lower for the 0.04 phospholipid to oil weight ratio lipid emulsion group relative to the 0.07 and 0.12 phospholipid to oil weight ratio lipid emulsion groups. This demonstrates that the initial elimination rate was fastest for the 0.04 ratio group. The data further illustrates a trend which indicates that steady state triglyceride levels are proportional to phospholipid to oil ratios and that the THM (time to reach ½ steady state) is greater for the 0.04 ratio group, which is consistent with the slower rise in triglycerides.

Figure 2:
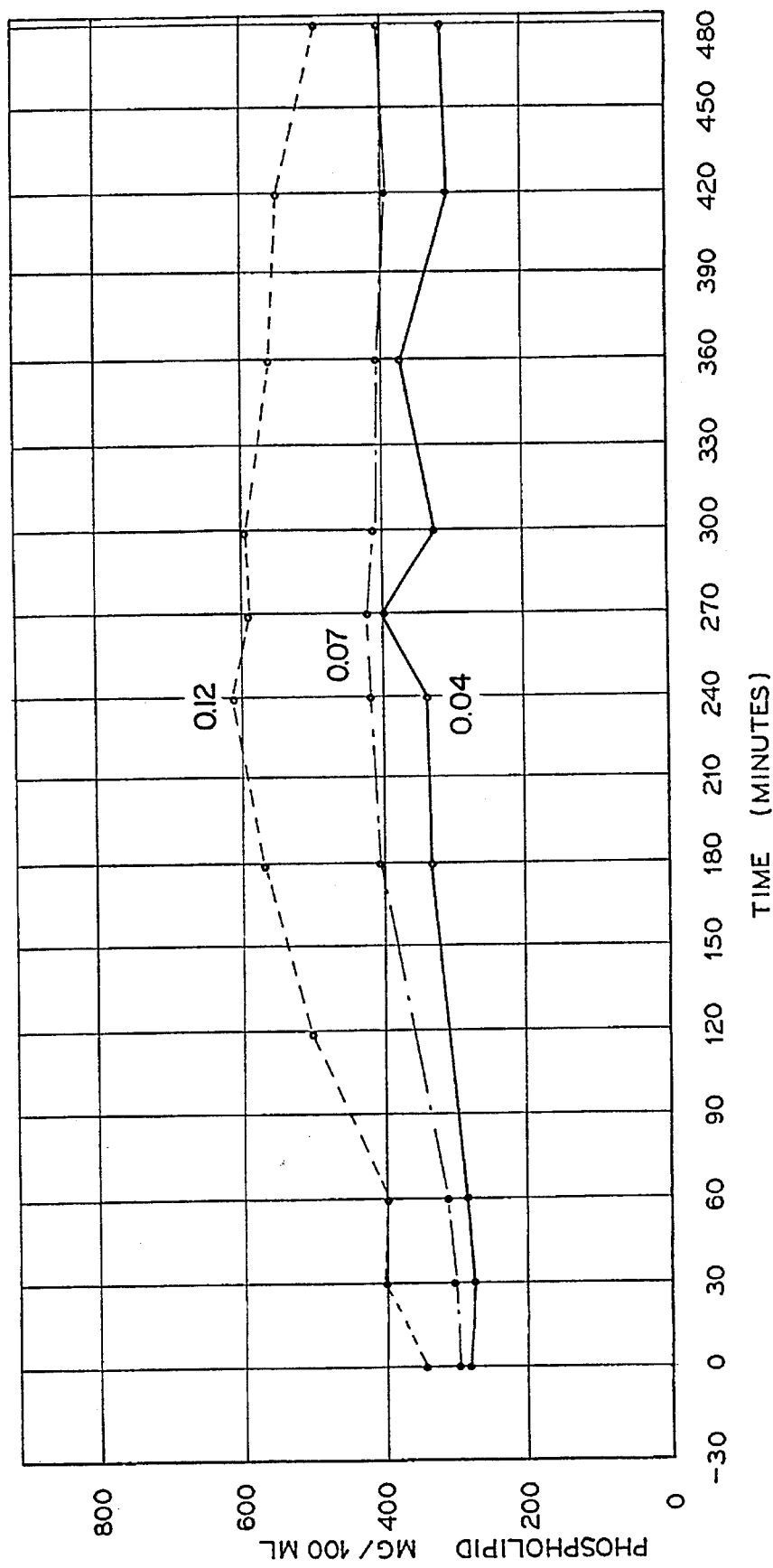
FIG. 2 illustrates a plot of the plasma phospholipid concentration versus time at different phospholipid to oil ratios.

An analysis of phospholipid concentration across time reveals that there was no significant difference between the 0.04 and 0.07 ratio groups. But, from 60 minutes to 8 hours the 0.12 ratio group was significantly higher than the 0.04 and 0.07 ratio groups. (See FIG. 2 that illustrates the phospholipid levels; again, 0.04 is represented by a solid line, 0.07 by a sectional line, and 0.12 by a dotted line.) Moreover, the data indicates that successive lipid emulsion infusions of lipid emulsions having 0.04 and 0.07 phospholipid to oil weight ratio will not cause a rise in the baseline levels of plasma phospholipids which was observed with the 0.12 phospholipid to oil ratio group.

The lipid emulsion particle size (particle volume-surface mean diameter) was also analyzed and is set forth in Table IV.

TABLE IV

| Sample Identification | Volume Surface Mean Diameters DVS(nm) |
|---|---|
| Emulsion with 0.12 phospholipid to oil ratio* | 204.5 |
| Emulsion with 0.07 phospholipid to oil ratio | 250.8 |
| Emulsion with 0.04 phospholipid to oil ratio | 268.6 |
| Mixture with 0.12 phospholipid to oil ratio | 197.7 |
| Mixture with 0.12 phospholipid to oil ratio | 204.7 |
| Mixture with 0.12 phospholipid to oil ratio | 196.2 |
| Mixture with 0.07 phospholipid to oil ratio | 241.3 |
| Mixture with 0.07 phospholipid to oil ratio | 240.3 |
| Mixture with 0.07 phospholipid to oil ratio | 249.2 |
| Mixture with 0.04 phospholipid to oil ratio | 281.0 |
| Mixture with 0.04 phospholipid to oil ratio | 278.1 |
| Mixture with 0.04 phospholipid to oil ratio | 270.4 |

*by weight

Particle size increased with a decreasing phospholipid to oil ratio. A large particle size is advantageous because it demonstrates maximum emulsification.

Figure 3:
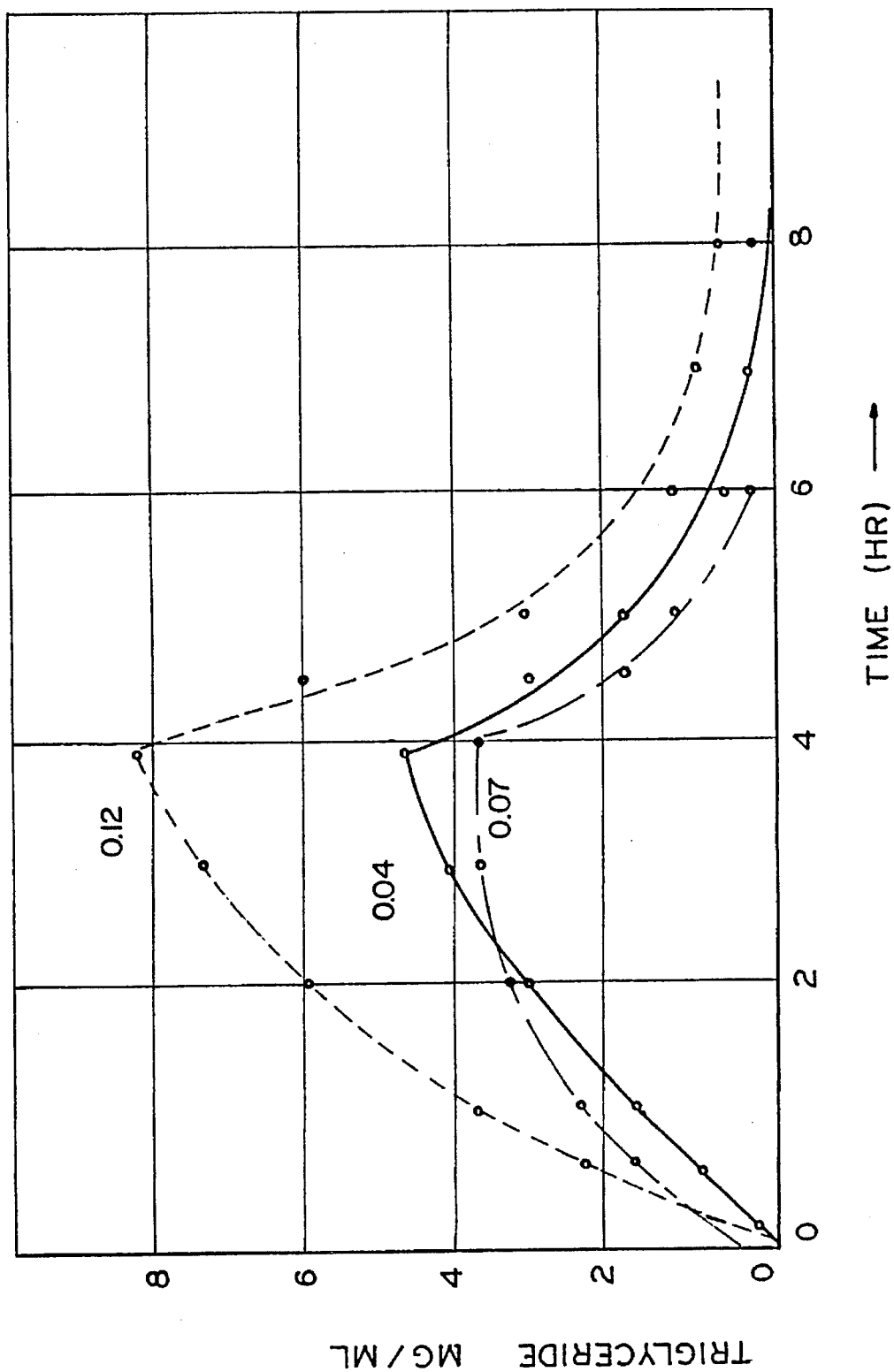
FIG. 3 illustrates a plot of the plasma triglyceride level versus time.

Each of the lipid emulsions was mixed with an amino acid solution, TRAVASOL, and dextrose and placed in plastic infusion bags. The solution was stored at room temperature for approximately 16 hours and then infused into beagle dogs over four hours. Five ml samples were then removed and stored at 4° C. until particle size was analyzed—approximately 6 weeks later. Visual examination indicated no breakdown of the emulsion and particle size analysis indicated no change had occurred. Tests indicate that plasma triglyceride levels were equivalent in dogs receiving this TPN solution over four hours when compared to animals receiving only lipids. The study established that metabolism of the lipid emulsion is enhanced by lowering the phospholipid to oil ratios and that moreover, the lipid emulsions having a low phospholipid to oil ratios are stable when mixed with a TPN solution, such as amino acids and dextrose. FIG. 3 illustrates a plot of the average concentrations for each lipid emulsion in the three in one infusion. Again, the 0.04 ratio solution is indicated by a solid line, 0.07 by a sectional line, and 0.12 by a dotted line.

Not only does the present invention provide an improved lipid emulsion for nutritional support, but, it also provides an improved lipid emulsion system for infusion of therapeutic agents. To this end, the present invention provides a lipid emulsion system capable of being utilized to infuse lipid soluble drugs. To overcome the unpleasant side effects associated with the intravenous injection of some drugs that are poorly soluble in water, it may be desirable to mix these drugs in a lipid emulsion. For example, Valium is typically mixed with co-solvents, such as alcohol and propylene glycol, that makes the intravenous infusion of Valium painful. However, Valium is a lipid soluble drug, and therefore, can be mixed in the lipid emulsion of the present invention and thereby, infused in a patient. Other agents that can be encapsulated in a lipid emulsion include, for example, antibiotics such as cephalosporin and antineoplastic drugs such as adriamycin.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method of treating a patient on total parenteral nutrition and preventing hyperlipidemia including the step of intravenously infusing into a patient a stable lipid emulsion including phospholipid and glyceride oil, the weight ratio of the phospholipid to glyceride oil being limited to approximately 0.04 to 0.01 so as to prevent the stable lipid emulsion from causing hyperlipidemia.

2. The method of claim 1 including the step of adding a lipid soluble agent to the lipid emulsion before the lipid emulsion is infused into the patient.

3. The method of claim 1 including the step of adding an osmotic agent to the lipid emulsion to produce an osmolarity of 280 to about 300 milliosmoles before it is infused into the patient.

4. The method of claim 1 including the step of mixing the lipid emulsion with an amino acid solution.

5. The method of claim 1 wherein the phospholipid is selected from the group consisting of: egg phosphatides; soybean phosphatides; and phosphatides of marine origin.

6. The method of claim 1 wherein the glyceride oil component is selected from the group consisting of: soybean; safflower; marine; black currant seed; borage oil; palm kernel oil; and coconut oil.

* * * * *